United States Patent [19]

Polson et al.

[11] Patent Number: 4,894,229

[45] Date of Patent: Jan. 16, 1990

[54] CARRIER-BOUND IMMUNOGENIC DETERMINANTS AND CARRIER THEREFOR

[75] Inventors: Alfred Polson, Camps Bay; Kirsten J. Van der Merwe, Stellenbosch, both of South Africa

[73] Assignee: South African Inventions Development Corporation, South Africa

[21] Appl. No.: 854,242

[22] Filed: Apr. 21, 1986

Related U.S. Application Data

[63] Continuation-in-part of Ser. No. 399,093, Jul. 16, 1982, abandoned.

[30] Foreign Application Priority Data

Jul. 17, 1981 [ZA] South Africa ...................... 81/4898

[51] Int. Cl.$^4$ .................... C12N 17/20; A61K 39/00; A61K 37/00
[52] U.S. Cl. ........................................ 424/92; 424/88; 424/93; 514/885; 514/2; 514/21; 435/132; 435/134; 435/131; 435/174; 435/176; 435/181; 435/820; 435/252.1; 435/252.8; 530/810
[58] Field of Search .................... 424/88, 92, 93, 85; 436/518, 519, 536, 532, 541, 819, 823; 435/4, 6, 7, 29, 253, 243, 820, 817, 245, 134, 132, 131, 176, 181, 174; 530/380, 810

[56] References Cited

U.S. PATENT DOCUMENTS

| | | | |
|---|---|---|---|
| 3,553,310 | 1/1971 | Csizmas | 424/2 |
| 3,639,558 | 2/1972 | Csizmas | 424/12 |
| 3,950,222 | 4/1976 | Takasaki | 435/174 |
| 4,057,685 | 8/1977 | McIntire | 424/88 |
| 4,320,194 | 3/1982 | Bull | 435/174 |

OTHER PUBLICATIONS

Galanos et al., *Eur. J. Biochem.*, vol. 24, pp. 116–1971, "Preparation and Properties of Antisera Against the Lipid A Component of Bacterial Lipopolysaccharides".

Dunlop, R. B., *Immobilized Biochemicals and Affinity Chromatography*, Plenum Press, N.Y., pp. 10, 11, 16, 17, 19, 20.

Weethall, H. H., *Immobilized Enzymes, Antigens, Antibodies, and Peptides*, Marcel Dekker, Inc., N.Y., pp. 15,16, 33–35, 438–445.

*Primary Examiner*—Robin Teskin
*Attorney, Agent, or Firm*—Millen, White & Zelano

[57] ABSTRACT

An immunogenicity increasing carrier substance for immunogenic determinants is composed of particles derived from gram-negative cells substantially devoid or depleted of their natural immunogenic determinants, more particularly prepared by stripping the O-antigen and core region off the lipid A by chemical cleavage (acid hydrolysis). These socalled "naked bacteria" are chemically treated with a linking reagent to provide covalently bonded intermediate linking moieties while preserving the adjuvant effect of the particles. The linking moieties have functional groups. These serve for the covalent bonding of selected haptens or antigens comprising the desired immunogenic determinants against which antibodies are to be elicited in living antibody-producing cells. Such carrier-bound immunogenic substance can be prepared in injectable form for immunizing fowls or mammals to induce protective immunization, or to produce specific antisera or to produce antibody preparations for diagnostic, forensic, pharmacokinetic and other tests.

43 Claims, No Drawings

CARRIER-BOUND IMMUNOGENIC DETERMINANTS AND CARRIER THEREFOR

BACKGROUND OF THE INVENTION

This is a continuation in part of Ser. No. 399 093 filed July 16, 1982.

The present invention relates to a carrier-bound immunogenic material or substance comprising immuno stimulating carrier particles and one or more immunogenic determinants for producing a desired specific immunogenic response in living antibody producing cells, the immunogenic determinants containing immunogenic information adapted to elicit the specific response, being attached to the exterior surface of a carrier in particle form. The invention also relates to a carrier substance for making the carrier-bound material.

The invention further includes a process for making such material and processes including the use of such materials.

In the present specification we use the term "immunogenic determinant" to denote a substance, molecule or part of a molecule which when present in an immunogen is responsible for a specific immune response when the immunogen acts upon an immune system, i.e. living antibody-producing cells. By "immune response" we mean that antibodies are formed by the immune system in response to an immunogenic stimulus elicited by the immunogen. The antibodies will include antibodies more or less specific to the immunogenic determinants (or combination thereof) of the immunogen. The term "immunogen" is used for a substance which elicits the formation of antibodies as aforesaid. The term "antigen" denotes a substance which couples with a matching antibody, thereby being bound and "neutralised" by the latter. In practice "antigens" and "immunogens" in a given context are often the same substances, for which reason the two terms are frequently used as synonyms.

A hapten denotes a usually small immunogenic determinant which only becomes an immunogen when coupled to a sufficiently large carrier for a given immune system. Different immune systems (e.g. of different animal species) differ in respect of the minimum size (or molecular weights) of immunogens to which they are able to respond satisfactorily. It will thus be understood that in certain instances an antigen may be able to couple with a given antibody yet may be too small to itself elicit the formation of such antibody in a given immune system. In that case, although the "antigen" possesses "immunogenic determinants" (or for that matter "antigenic determinants") specific to the antibody in question, such antigen is not an "immunogen" for the given immune system, but a hapten.

DISCUSSION OF PRIOR ART

Probably the oldest carrier-bound immunogenic determinant materials known in the past are complete bacterial cells. In the case of such cells the immunogenic information which elicits an immune response specific to such bacteria in the immune system of living organisms or cells (e.g. of animals exposed to infection by such bacteria or to innoculation with the dead but otherwise undamaged bacterial cells) is contained largely or wholly in the outermost layer or zone of each bacterial particle. In many bacteria, e.g. gramnegative bacteria such as salmonella, this natural immunogenic zone, constituting the "immunogenic determinants" of the bacteria, is largely or wholly confined to an outer layer or zone containing the O-antigens, i.e. the O-specific long chain polysaccharide immunogenic (antigenic) determinants, covalently bonded to a lipophilic, antigenically substantially inert surface of the cell wall of the bacterial particle. It was known that this antigenic determinant zone can be stripped off, e.g. by acid hydrolysis in the case of O-antigens resulting in "naked bacteria" which have substantially or wholly lost their natural characteristic immunogenicity. (C. Galanos, O. Lüderitz and O. Westphal; Eur. J. Biochem. 24 (1971), 116–122).

As described in that reference, gram-negative bacteria cells comprise an inner region surrounded by a cytoplasmic membrane, the outer periphery of which is known as the cell wall. The membrane is surrounded by a zone comprising a lipophilic substance known as lipid A. To the exterior of the lipid A in turn is bonded a socalled core region comprising generally a chain formed by a variety of sugar moieties (glucose, galactose, heptose and 3-keto-deoxy octonate (KDO)). Usually some of these sugar moieties carry substituents (phosphoethanol amine, phosphate, N-acetyl glucose amine). External to this core region is at least one and usually a succession of oligosaccharide units known as O-polysaccharides forming a continuation of the chain of the core region and constituting the primary sites of the natural immunogenic determinant regions of the cell. The entire region from the O-polysaccharides (also known as the O-antigen region) inward up to and including lipid A is known as lipopolysaccharides (LPS). The O-antigen region and core region can be stripped off the lipid A by chemical cleavage, in particular by acid hydrolysis, although enzymatic cleavage is also possible. With rare exceptions the O-antigens and the core region of gram-negative bacteria are covalently linked to lipid A by one or more KDO units which are readily split off the lipid A by mild acid hydrolysis without damaging the cell wall. What is left are cell particles which include the cell region ranging inwardly from lipid A to the inner region of the cell membrane, both inclusive, but from which natural O-antigen and core region have been largely or wholly stripped off. These are the particles which will herein be referred to as "naked bacteria". Usually (and preferably) the membrane is left intact, in which case these particles represent the complete (but killed) bacterial cells from lipid A inwards. Consideration has been given to the possibility of, after having stripped the O-antigens off such lipid A, applying to the resulting "naked bacteria" by adsorption onto the outer lipophilic surface thereof an amount of some other selected lipophilic molecules containing a desired specific immunogenic information. It had been hoped that this expedient would result in immunogenic materials of particularly advantageous properties. However, experiments which have led to the present invention have brought to light a number of unexpected drawbacks inherent in the aforesaid technique. Positive immunogenic results were attainable with some immunogenic determinant materials adsorbtively applied as aforesaid, but not with some others. One of the main drawbacks observed with the aforesaid method is the reversibility of the adsorption process. A lipophilic antigen will not only be adsorbed onto the naked bacteria, but also onto other lipophilic areas such as glass surfaces of laboratory equipment, the insides of plastics syringes and many lipophilic body constituents. This must be considered with the fact that immunogens are normally injected into test animals in the form of an aqueous suspension in buffer or physiological saline solution. Total desorption will result in a complete loss of immunogenicity and this may even occur in the body itself.

The aforesaid procedure is limited to immunogenic determinant substances having adequately strong lipophilic properties for being adsorptively bonded to the lipophilic carrier surface. If the substance to be used in the above proposed method is not lipophilic itself, it is necessary to first convert this into lipophilic derivatives, e.g. by coupling to stearic acid. Whilst this procedure was found to succeed with some desired immunogenic determinants, it was unsuccessful with other types of molecules (e.g. certain polypeptides), which suffered conformational changes after the addition of lipophilic chains. The lipophilic part of the immunogenic determinants as an inherent characteristic of the adsorptive bonding process, is necessarily drawn inside the adsorption complex, and desired immunogenicity may be lost in the process.

The adsorption of lipophilic molecules onto naked bacteria is also complicated by micell formation of lipophilic molecules in aqueous media which leads to uncertainties regarding the amount adsorbed.

Such adsorption complexes with naked bacteria are moreover unstable in the presence of adjuvants (e.g. Freund's adjuvant) which are often used for increasing the immune response.

For a variety of purposes to be explained more fully further below, it is necessary to produce antibodies against selected immunogenic determinants which in their existing form are incapable of eliciting any or any adequate immune response in a given immune system. This may be due to the molecular weight or particle weight of the substance including the immunogenic determinants being too small for the particular immune system. The minimum molecular weights for eliciting an immune response are different for different animals and different kinds of immune systems. According to Polson (West German Patent application No. P 29 51 412, Japanese patent application No. 54-73150, UK patent application 79 30764, U.S. Pat. No. 4 357 272) substances must have a molecular weight of more than 30 000 and preferably more than 100 000 in order to elicit a satisfactory immune response in fowls, suitable for transmission to the egg yolks of such fowls. This is important because according to the aforesaid references, such egg yolks can be used as an important source of antibody preparations. To mitigate this problem in certain cases (e.g. with snake venom components of comparatively low molecular weight) high molecular weight aggregates were formed by covalent cross-linking with cross-linking agents such as glutaraldehyde. The resulting improvement was not as large as hoped for. The cross-linking reaction could not be readily controlled very accurately. The effect of the increased molecular weight was in part offset by losses in immunogenicity due to losses of immunogenic groups as a result of the cross-linking reaction and high proportions of immunogenic structures becoming inaccessible in the interior of the aggregates.

Tne covalent linkage of immunogenic determinants onto protein molecules to serve as carriers, such as albumin or thyroglobulin, has been proposed (Methods in Immunology and Immunochemistry. Vol. I, page 120. C. A. Williams & M. W. Chase) but was found to similarly involve a number of disadvantages. Firstly, in order not itself to produce an immunogenic response, the protein selected as a carrier must in each case be derived from the same animal which is to be immunised. Such protein carriers are also not universally suitable, for all purposes or all immunogenic determinants, nor are the results predictable. Sometimes it is found that antibodies are raised predominantly or wholly against the protein antigen rather than the desired immunogenic determinant. Also the structure of the immunogenic determinants must be taken into account. For example, if certain immunogenic determinants, in particular those of lipophilic character, are grafted covalently onto a protein, the structure changes so that the lipophilic part becomes wrapped up and shielded inside with resulting loss of immunogenic response to that particular part of the immunogenic determinant.

The use of microbe cell particles as carrier particles for proteins and other materials such as enzymes, lectins and more particularly antigens and antibodies has been described by Bull in U.S. Pat. No. 4 320 194 in the context of agglutination tests. The use of such particles for challenging antibody producing cells is neither described nor suggested, and indeed the procedures described in that reference, designed to produce reagents of high specificity in agglutination tests, for that very reason teaches away from methods suitable for producing an immunogenic substance of enhanced immunogenicity (which is the purpose of the present invention). The preferred microbe cells are yeast cells which are treated with a cross linking agent and a stabilising reagent such as epihalohydrin epoxide, whereby tne particles are rendered substantially as inert as plastics micro beads and can make no positive contribution to any desired immune response. Similar techniques have been employed for the production of immobilised enzymes on micro organic cells (U.S. Pat. No. 3 950 222 granted to Takasaki). Both fields of application are covered by similar techniques in accordance with U.S. Pat. Nos. 3 553 310 and 3 639 558 to Csizmas et alia. Here the formation of insoluble reactive particles is taught by the treatment of bacteria with reagents such as glutaraldehyde, followed by coupling immunological material to the carrier particles so formed. The carrier particles are to be used as 1. an immuno reagent to test for an immunological counterpart thereto
2. an immuno adsorbent
3. an enzymatic conversion reagent and
4. an indicator particle for agglutination tests.

According to these references the carrier particles are "insolubilised" in the sense of being "stabilised and preserved against lysis". They will accordingly not be broken up in vivo to expose the various natural parts of the carrier particles to the immune system, nor will they be readily eliminated from the system. The particles are treated with acrolein which forms a complete, solid, polymerised, insoluble coating. This coating is chemically activated and the antigen is then linked to the outside of the activated coating and not to the cell material as such. As in the previously cited examples the particles are rendered substantially as inert as are plastics micro beads. Quite clearly the use of the substances described by Csizmas et al as immunogenic substances for challenging antibody producing cells is neither described nor contemplated, the described procedures being such that they destroy all properties of the particles which might otherwise enhance immunogenicity.

The use of bacteria and bacterial products as immunostimulants has been known for some time, a well known example being Freund's adjuvant. The use of bacterial products ranging from whole cells to various cell fragments, as immuno modulating agents is summarised in a monograph by G. Gialdroni-Grassi, Int. Archs Allergy Appl. Immun. 76: Suppl.1, pp. 119–127 (1985). In general these products, when used as adjuvants, are either administered separately from the substance containing immuno determinants against which antibodies are to be elicited, or a physical mixture of such bacterial products and the substance used for challenging the immune system is prepared and administered. Covalent conjugates of antigens or haptens with bacterial products having immuno stimulating properties have been confined to bacterial products of modest molecular weight and limited immuno enhancing properties. For example, in U.S. Pat. No. 4 057 685 to MacIntyre conjugates of a partly detoxified derivative of LPS (see above) are described to produce an improved immune response.

Chedid et al (mol immunol 1980, 17, No 3,357-63 have described synthetic vaccines comprising covalent conjugates of muramyl dipeptide derivatives (MDP) and haptens or antigens. MDP is a peptide component of cell walls of bacteria. All of these procedures result in particles of relatively small size. Conjugation to larger carrier molecules should therefore be resorted to. Only a very specific selected portion of immuno-stimulating sites of the cell is utilised, a factor recognised by the present inventors. Problems of toxicity and anaphylactic shock also apparently have been dealt with only to a limited extent. Also, for example, if LPS or an LPS derivative is used as a carrier, the conjugate acts as a T cell independent immunogen. This limits the carrier to operating via this particular mechanism and limits the response of the immune system.

THE INVENTION

Quite generally, it is an object to improve the immunogenic response to a given immunogenic determinant in a given immune system. This applies to the quantity and/or to a desired quality of antibodies formed, in particular the avidity (antigen affinity).

More specific objects pertaining to the respective aspects of the present invention include to provide an immunogenic material as aforesaid, w herein (if necessary after comparatively simple optimising trials) a relatively high immunogenic activity is conferred to immunogenic determinants (haptens) of relatively low activity or no activity, which has superior stability and shelf life, which lends itself to improved controlled and standardised manufacture, which is applicable to an exceptionally wide range of immunogenic determinants and is readily tolerated by organisms in which an immunodigenic response is to be elicited therewith. In particular the present teachings are to show way and means by which the amounts of immunogenic determinant grafted onto a carrier can be controlled, as well as the immunogenic characteristics (chemical groupings). which after such grafting remain available and exposed in a manner suitable to elicit an immunogenic response.

The present invention is based on the concept of an immunogenic material or substance as aforesaid comprising as a carrier substance gram-negative bacterial particles denuded of their natural O-antigen and carrying grafted onto their outside by covalent bonding an immunogenic determinant containing immunogenic information which elicits the specific response.

According to one aspect of the invention, there is provided a carrier substance for immunogenic determinants, comprising immunogenicity increasing carrier particles derived from gram-negative bacterial cells substantially devoid or depleted of natural immunogenic determinants of the cells and comprises that region of the cells which includes lipid A and from there ranges inwardly towards the cell interior and including cell wall material, the particles having been chemically treated with a linking reagent to provide covalently bonded intermediate linking moieties exposed on the particles, providing reactive functional groups adapted to be bonded covalently to selected haptens or immunogens comprising immunogenic determinants as aforesaid.

More particularly the particles are gram-negative bacterial cell particles subjected to chemical cleavage to substantially free the lipid A of O-determinant-carrying material external of the lipid A, followed by covalent bonding to the particle exterior of the intermediate linking moieties.

Preferably the cell walls of the cell particles are substantially intact.

The linking moieties should be present in amounts adapted to bond the required or preferred amounts of hapten or antigen (serving as source of the selected determinant(s) as set out more fully further below Also in accordance with the invention, there is provided an immunogenic substance with inherent adjuvant properties, comprising immunogenicity-increasing carrier particles having an exterior surface, derived from gram-negative bacterial cells having a membrane including an outer periphery known as the cell wall and lipid A, which particles include the cell region ranging inwardly from lipid A to the membrane, both inclusive and from which particles any cell material beyond lipid A, including O-antigen has been removed by chemical cleavage wholly or predominantly and further comprising an immunogenic determinant for producing a desired immunogenic response in living, antibody-producing cells, the determinant being covalently bonded by a synthetic linking reaction to the exterior surface of the carrier particles in a form permitting immuno recognition by antibody-producing cells, the immunogenic determinant containing immunogenic information which elicits a desired response.

The scope of the invention extends to immunogenic compositions, e.g. vaccines, comprising such material or substance as aforesaid, if desired or required, mixed with a suitable diluent or extender substance, more particularly in a form suitable for administration as a vaccine and containing the substance or material in an immunologically effective amount, for example dissolved or suspended in the form of a parenteral solution or suspension.

More particularly, the immunogenic determinant so covalently bonded is present in addition to or instead of immunogenic determinants naturally present as a component of the carrier bacterial particle and the carrier material particle includes at least the cell wall region, including the cytoplasmic membrane of the bacterial cell.

In the majority of embodiments of the invention the immunogenic determinant which is thus covalently bonded, is itself foreign to the bacterial particles onto which it has been grafted. In fact there is almost no limit to the variety of such determinants (of small or large molecular weight) which can be thus grafted to the bacterial carrier particles.

However, the invention also contemplates stripping gramnegative bacteria of their natural O-determinants and then covalently bonding such O-determinants or a selected portion or region thereof carrying desired immunogenic information back onto the resulting "naked bacteria", e.g. in optimised amount or configuration to achieve an optimised immune response.

Covalent bonding in the present context is intended to include dative, co-ordinate bonding. However, in the preferred embodiments simple covalent bonding, such as results from common condensation reactions applies.

Further aspects of and preferred features of the novel material will become apparent from the description of the process in accordance with the invention for manufacturing it and the description by way of example of certain preferred embodiments.

Also in accordance with the invention, there is provided a process for producing an immunogenic material as aforesaid, wherein a selected immunogenic determinant is grafted onto a carrier, comprising the feature that the immunogenic determinant is grafted by a covalent bonding reaction or reactions onto the exterior surface of the above-defined bacterial particles, i.e. naked bacteria, serving as carriers.

The aforesaid naked bacteria serve as immunogenically substantially or wholly neutral carriers (at least in some animals) for the hapten or immunogen covalently bonded thereto. The immunogenic response elicited by the substance or material according to the invention is thus confined wholly or predominantly to the selective formation of the desired antibodies against the selected immunogenic determinant, the response being attenuated by the effect of increased size due to the conjugate formation as well as a pronounced adjuvant effect inherent in the bacterial particles. The result is that the combination of such carriers with the immunogenic determinant elicits a superior immune response to such determinant.

Quite surprisingly the improvements observed often exceed by far those to be expected from a mere increase in particle size of the immunogen. Great improvements—with regard to yield of antibodies as well as the quality thereof i5 (particularly in respect of avidity, i.e. the intensity in terms of speed, capacity and complexing strength with which antigens are captured by the antibodies)—are observed even with substances of high molecular weight and which already possess good immunogenic properties by conventional standards, once these substances are grafted covalently onto naked bacteria. (See also U.S. Pat. No. 4 550 019 to Polson). The improvement is often substantially greater than can be explained by particle size alone. There occurs also a synergistic effect due to properties inherent in the bacterial particles. Possibly this is due to a natural adaptation of immune systems to recognise and respond to immunogens having bacterial characteristics as part of the body's defence against bacterial infection. The bacterial carrier particles thus act as a built-in adjuvant which tends to improve the speed with which antibodies are formed in response to challenging with the novel immunogen, as well as the yield and quality of the antibodies.

As explained in the discussion of the prior art, it is known that some bacterial cells and also certain specific chemical moieties or structures occurring in the cells possess pronounced adjuvant properties, but in the past only individual such moieties or structures, in particular muramyl dipeptide (MDP) and lipo-polysaccharides (LPS), have been bonded covalently to form immunogenic conjugates with haptens or antigens. Severe toxicity problems were experienced which have been overcome only in part by various detoxifying procedures. The surprisingly strong adjuvant effect observed with naked bacteria is probably due at least in part to the fact that in naked bacteria there is present a combination of large particle size (thus obviating the need for additional carrier molecules as in the case where MDP is used alone), pl us the full spectrum of immuno-stimulating substances known to exist in bacterial cells, namely MDP, lipid A (which has been identified as the real active moiety of LPS molecules) and endotoxin protein as well as certain outer-membrane proteins (OmpA, F and C) and possibly others not yet identified. Due to the natural O-antigens having been stripped off, these are eliminated as unneeded and undesirable antigenic determinants, since Oantigens depress the immuno-stimulating effect of lipid A. Moreover, the immuno-stimulating lipid A can be rendered more accessible. The covalent bonding reactions (e.g. using linking agents such as glutaraldehyde) can achieve a partial detoxification of the lipid A (in those cases where it is toxic). More important even, the toxicity (if any) of lipid A in naked bacteria is already reduced by a factor of about 200 as compared with free lipid A, simply as a result of the large particle size.

In many cases it is found that the immunogenic effect of haptens or immunogens is stimulated so much by their being bonded to naked bacteria that only very small amounts of the desired immunogenic determinants are needed. This is important if the determinants are expensive or are only available in very small amounts.

The naked bacteria by virtue of the chemical composition of their surface offer a wide choice of reactive groups whereby these particles can act as substantially universal carriers. Moreover, it is found that in general a very good immune response is obtained with the conjugates according to the invention, probably at least in part due to these particles constituting a kind of natural (biological) carrier system to which higher living organisms are accustomed and attuned. This is so, because bacteria in the alimentary tract and similar environments in living organisms are continuously subjected to degradation, yielding materials having much in common with the aforesaid "naked bacteria". This may also explain why in some higher organisms tested, e.g. hens, these "naked bacteria" were found to be totally or substantially immunogenically inert, i.e. incapable of by themselves eliciting the production of antibodies. In view of this observation, the particularly strong immunogenicity imparted onto otherwise immunogenically weak or inert immunogenic determinants, once they have been grafted onto these themselves immunogenically inert particles, was not to be predicted, particularly not in view of some disappointing results previously observed with the same or similar determinants covalently grafted onto other carriers such as proteins of high molecular weight. The observed improvements resulting from the invention often exceed those of conventional adjuvants by far. The present process can be visualised as resulting in immunogenically ideally shaped and dimensoned carrier particles which carry on their exterior surfaces a relatively even distribution of the covalently bonded determinants. It is probable that this even distribution is an important factor which promotes the formation of antibodies of high avidity and high specificity in response to the product of the process. Such even spacing is likely to stimulate a narrow range of antibody-producing cells. This in turn results in a narrow spectrum of antibodies which have improved specificity (similar to monoclonal antibodies—without the effort and cost involved in monoclonal techniques) and often have high avidity. (The avidity is mathematically expressed as the "K-value" which equals the reciprocal of the free antigen concentration when half the antibody binding sites are occupied by antigen. The term "affinity" can be used instead of "avidity" in the case of antigens which are so small that they can each bind ( only one antibody. K-values of $10^4$–$10^5$ L/mole indicate a low avidity, whilst K-values of $10^{11}$–$10^{12}$ L/mole are considered very high).

In the preferred embodiments of the present invention involving naked bacteria, the bacteria are of a type wherein the antigenic determinant zone is readily stripped off.

The scope of the invention is not limited to naked bacteria derived from any specific gram-negative bacteria family, species or strain. The bond(s) next to the lipid should be readily hydrolysable, preferably without damage to the cell wall. All gram-negative bacteria which have KDO linked to lipid A are particularly suitable because of the ease with which the ketosidic linkage between the O-determinants and the lipid is cleaved (C. Galanos, M. A. Freudenberg, O. Lüderitz, E. T. Rietchel and O. Westphal: Biomedical applications of the Horseshoe Crab, Alan R Riss, Inc. 150 5th Avenue, New York, pages 321 to 332) by mild acid hydrolysis with dilute organic or inorganic acids such as acetic or hydrochloric acid, e.g. with 1% acetic acid. These include the entire family of Enterobacteriacea and particularly the following:

Genus Escherichia
Genus Salmonella
Genus Shigella
Genus Klebsiella
Genus Enterobacter
Genus Serratia
Genus Proteus
Genus Erwinia Particularly good results have been attained with strains having relatively small amounts of natural antigenic determinants present on the bacterial surface, e.g. S. minnesota R595. However, good results have also been attained with E. coli, e.g. the strain E H 100 or with S. abortus equi. which are readily and cheaply available.

Other gram-negative bacteria which are considered very suitable are the following:

Family Rhodospirillaceae: specifically
  Genus Rhodospirillium
  Genus Rhodopseudomonas
  Genus Rhodomicrobium
Family Chromatiaceae
Family Pseudomonadaceae
Family Azobacteraceae
Family Vibrionaceae
Family Bacteroidaceae All of the above are considered acceptable in the form of naked bacteria, because naked bacteria are dead and have no pathogenicity, moreover, to the extent that they are toxic at all, such toxicity is greatly reduced for reasons stated further above. .Moreover, in specific cases where toxicity is considered important (some animals being insensitive to the toxicity of lipid A), persons skilled in the art are readily able to avoid those bacteria which are known to have a high toxicity.

In this context the Family Rhodospirillaceae is preferred because its members, e.g. Rhodopseudomonas, spheroides possess non-toxic lipid A but still have strong immuno-stimulatory properties.

The chemically reactive groups which are made available by stripping off the outer layer, e.g. O-antigens, include amino, carboxy, phenolic hydroxy, alcoholic hydroxy. thiol and similar groups typically present in such bacterial material.

Accordingly, the process according to the invention comprises first stripping off the natural immunogenic determinants of bacterial cells, and then causing exposed covalently reactive sites on the bacterial particle surfaces to enter into covalent bonding reactions with a selected immunogenic determinant.

It is usually not necessary for the natural O-determinants to be stripped off completely. For most purposes naked bacteria are considered satisfactory if at least 80%, preferably at least 90%, say from 92 to 98% of the natural O-antigens have been cleaved off.

In most embodiments of the substance or material and process according to the invention, the selected immunogenic determinant in effect replaces the immunogenic function of the naturally present antigenic determinants of the bacterial particles.

The covalent bonds are much stronger than adsorption bonds, whereby the disadvantage of the adsorption method, wherein the immunogenic determinant tended to be split off is avoided. The prior art uncertainties which arose with adsorbed lipophilic immunogenic determinants are avoided. The desorption problems which arise when lipophilic immunogenic determinants adsorbed on a carrier are injected in an oil supension are avoided when the immunogenic determinant is covalently linked to "naked bacteria".

The amount of immunogenic determinant applied to a given amount of naked bacteria serving as a carrier can readily be standardised when the immunogenic determinant is covalently linked instead of being adsorbed onto the naked bacteria.

The afore-defined process in accordance with the invention is preferably conducted with the aid of one or more bifunctional linking reagents having two functional groups of which at least one is covalently reactive to enter into a bonding reaction with a reactive site of the bacterial particle whilst at least one other functional group is reactive to enter into a bonding reaction with a reactive site of the immunogenic determinant or a molecule carrying the determinant.

The at least two functional groups of the linking reagent may be identical or different. If they are different, the one group may be specifically selected to react with a specific type of reactive site on the bacterial particle, whilst the other may be specifically selected to react with a specific type of reactive site on the immunogenic determinants. Many immunogenic determinants are likely to have several types of reactive sites, of which some are likely to be more involved than others in the peculiar and specific immunogenic activity of such determinant, i.e. more specifically involved in eliciting an immune response specific to that determinant. For that reason the choice of site most suitable for bonding the immunogenic determinant to the bacterial particle, whilst preserving a maximum of specific immunogenic activity of the determinant should be made with due regard to this principle, if necessary by simple experiment with different linking reagents. Typical functional groups of linking reagents are

| Functional groups | Reacts with |
|---|---|
| Aldehyde | primary amines |
| Imide | primary amines |
| Amino | aldehyde |
| Cyano | hydroxyl groups |
| Halogen (e.g. bromine) | thiol groups |
| Carboxyl groups | primary amines |
| Activated carboxyl groups (e.g. N—Succinimidyl esters of carboxylic acids)(*) | primary amines or hydroxyl groups |
| Anhydrides (e.g. Succinic anhydride and maleic anhydride) | primary amines |
| Maleimide derivatives | thiol groups |

(*)e.g. N—hydroxy succinimide ester of N—(-4-carboxycyclohexyl methyl)-maleimide.

Preferred examples of such linking reagents are :
Dialdehydes, in particular aliphatic dialdehydes, preferably glutaraldehyde and its higher homologues having from 4 to 20 carbon atoms; separating the aldehyde groups;

Diamines, more particularly compounds wherein the amino groups are separated by from 2, preferably 4 to 20 carbon atoms, e.g. hexamethylenediamine;

Cyanogen bromide. It reacts in the first step with the -OH groups of the sugar residues of the polysaccharide cell wall components to form activated imido esters which in turn react in the second step with the amino groups of the antigens.

Further preferred linking compounds are described in the specific examples.

The aforesaid linking reagents may be caused to react with the respective reactive sites in manners known per se, more particularly as set out in the aforegoing table.

In preferred embodiments of the process, the linking reagent is first reacted with one of the two partners to be grafted together to form a reactive intermediate which is then reacted with the other partner. The first said partner may be either the immunogenic determinant or the bacterial particle.

An immunogenic determinant containing a hydroxyl group can be conjugated by the following means. As an example one could take β-ecdysone, a steroid which contains an OH group which is not immunogenically important.

Firstly, the naked bacteria is to be succinylated so as to react with the amino groups on the surface:

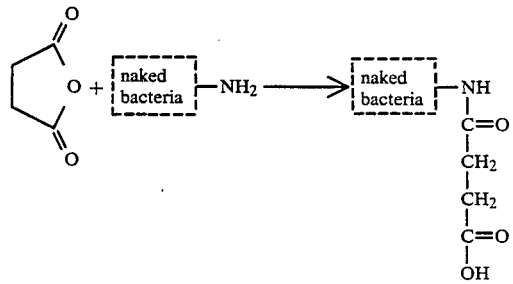

This effectively changes these amino groups so carboxyl groups which are then used in the next step.

The naked bacteria intermediate and the β-ecdysone are then esterified, e.g. with 1-ethyl-3-(3-dimethylaminopropyl) carbodiimide hydrochloride and an acylation catalyst such as 4-dimethylaminnopyridine as follows:

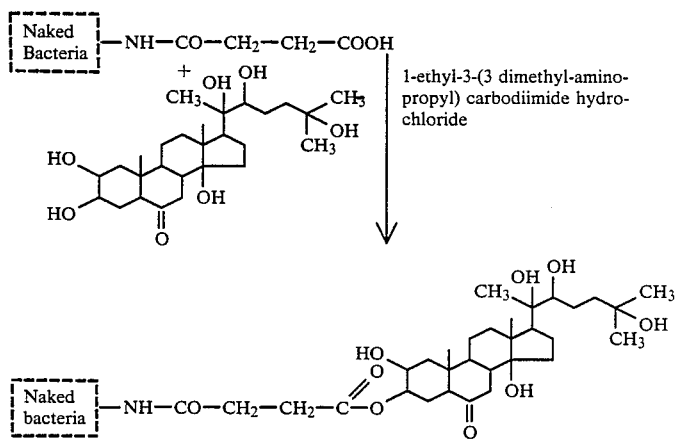

β-ecdysone naked bacteria conjugate.

Alternatively, both partners may each be reacted (e.g, seperately) with a linking compound to form reactive intermediates which intermediates in turn are then reactively bonded together.

In order to avoid undesirable cross-linking of either the immunogenic determinant or the bacterial particles, it will be advantagous to employ a linking compound having two different functional groups one group being selective for the reactive sites of the immunogenic determinants and the other being selective for the reactive sites of the bacterial particles.

An example of such a reagent is N-succinimidyl-3(N succinimidyl proprionate. This reagent is used to bind to the naked bacterial determinant that has a -SH group as follows:

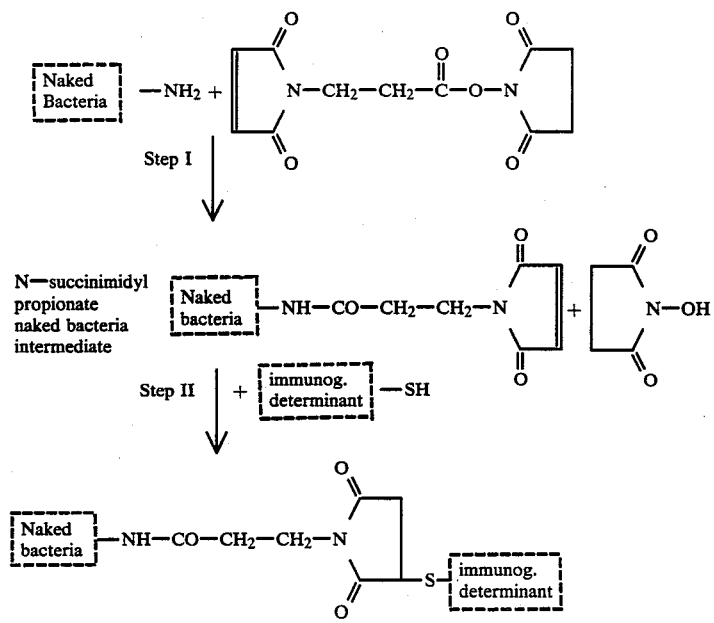

naked bacterial/determinant conjugate

If either the determinant or the bacterial particle or both lack a reactive group suitable for the covalent bonding reaction with the bifunctional linking compound, a reactive derivative is formed by introducing such reactive group by an appropriate reaction, e.g. with a different bifunctional linking compound. The same applies if it is considered undesirable to sacrifice any of the existing reactive groups of the antigen for the bonding reaction, because their preservation is considered important for a desired immune response.

It is preferred for reasons of geometry and improved immune response to select a linking compound or compounds adapted to provide a relatively long linking chain, e.g. an aliphatic carbon chain of preferably at least 3, up to about 20, more preferably from 4 to 10 carbon atoms between the immunogenic determinant and the bacterial particle.

Preferably the amount of any particular immunogenic determinant grafted onto a given amount of given bacterial particle materials is carefully controlled according to the following criteria:

1. The maximum amount of linking compound and/or immunogenic determinant which can be bonded so that it cannot be washed off again, is determining empirically.

This may be done by a kind of titration procedure involving any suitable mode of determining directly or by deduction the amount of reagent actually consumed. Use may be made of reagents labelled with a radioactive tracer. It is possible to measure the amount of radioactivity firmly bound; alternatively the "titration end point" beyond which the radioactive tracer will appear in the washing liquid is determined.

2. the following conditions must be complied with for the conjugates to be effective:
   (i) A minimum number of immunogenic determinants per unit of surface area must be present (this is related to mass of substance per mass of naked bacteria);
   (ii) The amount of immunogenic material should preferably not be so large that there is mutual steric interference between individual determinants (this amount is a function of total weight of immunogenic material as well as molecular dimensions and structure)

3. The optimised immunogenic activity is attained before the surface of the particles reaches a stage of "overcrowding". This stage is best determined for a given determinant by a simple series of routine experiments, e.g. with chicken hens (preferably of the same variety as those to which the carrier-bound determinant is subsequently to be applied). The immunogenic response is related to geometric factors which determine the accessibility to the immune system of the immunogenically active sites.

4. If a maximum immunogenic response is not critical, the grafting is carried out with a limited amount of determinant which according to experience is likely to be less than the maximum bonding capacity of the carrier particles.

One might have expected that in the context of criteria 2(ii) and 3 set out above, the suitable and preferred mass ratios of immunogenic determinant substance to carrier substance would have to vary quite substantially depending on the molecular mass, dimensions and structure of the immunogenic determinant substance. Surprisingly it is found that the effects are mutually compensatory to a substantial degree so that it is possible to lay down mass ratios which are reasonably universally applicable, regardless of the molecular mass or particle mass of the hapten or immunogen to be bonded covalently to the carrier particles.

Thus, it can be said that as a general rule the amount of hapten or immunogen to be covalently bonded to the bacterial carrier substance should be from 1 to 2 $\mu g/mg$ bacterial particles upwards, more particularly in the range of from 1 to about 200 $\mu g/mg$ on a dry mass basis, preferably 5 to 50 $\mu g/mg$. Where the carrier particles are premanufactured by treatment with a linking reagent, the amount of linking reagent covalently bonded is determined according to the same criteria, i.e. for the carrier substance to be adapted to bond/typical haptens or immunogens in the aforesaid amounts.

Typical preferred loads of hapten or immunogen per mg of bacterial carrier particles on a dry mass basis are the following (determined for "naked" Salmonella minnesota R595, dried in vacuo, but essentially applicable also to other "naked" bacteria):

Trinitrophenol (TNP) (molecular weight=213) 5-25 µg/mg preferably 15 µg/mg.

Triiodothyronine (molecular weight 651) to 20 µg/mg, preferably 5 µg/mg.

Thyroxin (i.e. T4, also known as tetraiodothyronine—molecular weight 776,9) 1 to 20 µg/mg, preferably 5 µg/mg.

Cobra venom (Naja nivea, molecular weight 3000-30 000; 20 or more components) 6 to 30 µg/mg, preferably 12 µg/mg.

Serameba antigen 4-20 µg/mg, preferably 8 µg/mg.

TSH (thyroid stimulating hormone - molecular weight 25 000) 5to 25 µg/mg, preferably 10 µg/mg.

Typical steroids (approx. molecular weight 325) 5-25 µg/mg, preferably 15 µg/mg.

Cholera antigen (molecular weight 90 000) 5 to 50 µg, preferably 20 µg/mg.

In preferred embodiments of the invention each mole of immunogenic determinant is bonded to the bacterial particles with between 1 and 3 moles of bifunctional linking compound.

It will be readily understood by those skilled in the art that departures from such calculated or estimated first approximation will depend inter alia on factors such as number, chemical character and geometry of those chemical groups or molecular regions of an immunogenic determinant which most strongly elicit a desired specific immune response, as well as the extent to which active immunogenic groups or molecular regions are lost due to the bonding reaction or unfavorable geometric positioning.

From the introduction to the present specification and also from the uses of the invention which are to be described further below, it will be readily apparent that there are very few limitations if any, as regards the types of immunogenic determinant to which the invention can be applied.

The invention was initially primarily intended for the grafting of immunogenic determinants too small by themselves to elicit a satisfactory immune response in a given immune system. This applies primarily to immunogenic determinants having a molecular or particle weight of less than 150 000, more particularly less than 100 000, and especially those less than 30 000 daltons. As regards the lower molecular weight limit, it is to be understood that "immunogenic determinants" for purposes of the present invention may even include small fragments of a particle or molecule as long as they contain the specific immunogenic information in response to which it is desired to elicit the formation of highly specific antibodies. Accordingly, the lower limit will be the lowest molecular weight of any molecular fragment or grouping which can give rise to any specific and characteristic immune response.

For example, in the case of substances such as T3 or DTP, the lower limit is represented approximately by fragments including three amino groups.

However, the invention also offers important advantages even with immunogenic determinant molecules or particles of relatively high mass, i.e. sufficiently large to elicit an immune response by themselves. It has been observed that the use of the invention elicits the formation of antibodies of superior quality in respect of their physical and immune properties. The antibodies carry a particularly high charge. They are more stable and better suited for binding studies than those having lower isoelectric points. The avidities of the antibodies are generally high. The antibodies are in fact to be considered new or improved products according to the invention because they are clearly different in respect of the aforegoing properties sometimes by orders of magnitude.

The bacterial nature of the carrier substance and the uniform distribution of the immunogenic determinants on the carrier surface all contribute to the desirable quality characteristics of the antibodies and good yields.

Example of haptens or immunogens to which the invention may be typically applied are :

Pathogenic or non-pathogenic microbes, e.g. too small to elicit a satisfactory immune response in their non-grafted form and fragments thereof, including relatively small viruses, fragments of viruses and so-called viroids.

Venoms, e.g. of snakes, spiders, scorpions, insects, poisonous fish or molluscs; toxins, poisons, drugs, hormones.

Antibodies or other body substances which are symptomatic of a pathological condition, e.g. an active infection or past exposure to a disease, or against which antibodies are needed for any purpose whatsoever, e.g. for the manufacture of carrier-bound (immobilised) immunosorbents. In this regard reference is made to the disclosure of U.S. Pat. No. 4,479,946. The relevant teachings of that patent are to be considered as part of the present disclosure.

Strands of RNA or DNA or specific fragments thereof. Enzymes or specific enzyme fragments. Any substances containing immunogenic information suitable for qualitative or quantitative forensic, pathological or analytical investigations.

The immunogenic products manufactured according to the present invention may be put to a large variety of uses. Such uses include the active immunisation of animals or humans for protection against disease. This may be done by injection (subcutaneous, intravenous, depot) or by oral or nasal administration, e.g. inhalation in the form of a spray. or aerosol. These procedures are known per se and require no description. The particularly high degree of compatibility of the carriers used according to the invention with the body systems of animals and humans is a particular advantage.

Active immunisation as aforesaid, may also be applied, substantially in manners known per se to the manufacture of antibody preparations, e.g.

(a) for use in passive immunisation or anti-venom treatment (anti-sera)

(b) for use in the manufacture of so-called "diagnostics". This term includes uses such as the identification and qualitative or quantitative assessment of pathological conditions in animals, humans and plants, the identification and determination of microbes (including bacteria, viruses and viroids) whether pathogenic or not, in biological or any other samples (e.g. water, effluents or soil); identification and quantitative assessment of toxins, poisons, drugs in body fluids, tissues or any other samples, tissue typing, identification of sources of biological samples; forensics; criminal pathology and specialised analytical work.

(c) For use in the immunological extraction, concentration and purification of substances from solutions, e.g. concentration/purification of highly specific members of an antigen/antibody pair. Once again the principles underlying such uses are well-known to persons skilled in the art and require no further description.

(d) The manufacture of immobilised immune preparations. For this use as well, the principles, techniques and procedures can be those which are known in the art.

For any one or more of the aforesaid purposes the present invention teaches appropriate immunisation methods in order to raise desired antibodies against the specific immunogenic determinants of the immunogenic material according to the invention, and such methods and applications are considered within the scope of the present invention.

In a general way this aspect of the invention may be defined as a process for the manufacture of antibody preparations which comprises challenging antibody producing living cells with a carrier-bound immunogenic determinant material according to the invention to elicit the production of antibodies against the determinant(s) of such material and optionally and preferably concentrating the antibodies.

Where the immunisation is applied to mammals (e.g. rabbits, guinea pigs, rats, pigs, horses, sheep) the immunisation regimen may be adapted from any appropriate procedure known per se, with or without the use of an adjuvant (e.g. Freund's adjuvant or incomplete adjuvant).

The sera of such immunised animals may, if desired, be collected and processed for the recovery of antibody products in a manner known per se. The increased molecular or particle weight added to the immunogenic determinants according to the teachings of the present invention, the configuration of the particles and the manner in which the determinants are distributed on the exterior of the particles have a favourable effect in many cases on not only the quantity, but also the quality of the antibodies raised. Antibody preparations manufactured in accordance with the invention are to be considered within the scope of the present invention.

Particularly preferred embodiments of processes wherein the immunogenic material according to the invention is used for the manufacture of antibodies comprise the immunisation of fowls in a manner known per se and the recovery of antibody preparations in a manner known per se from the serum of such fowls, but more preferably from the eggs of such fowls and in particular from the egg yolk. In this respect the teachings according to U.S. Pat. Nos. 4,357,272 and 4,550,019 apply, which by reference thereto are to be considered a part of the present disclosure and need not be repeated here.

The present invention offers particular advantages in the context of immunising fowls for producing IgY from egg yolk. As has already been explained above, the immune response in egg yolk to any immunisation of hens with immunogenic determinant material having a molecular weight below 30 000 is usually either negligible or absent and is usually weak or even absent even in the case of immunogenic determinants having a molecular weight below 100 000. This phenomenon may be utilised in practice, since it renders such egg yolk very selective in that the introduction of antibodies into the egg yolk in response to immunogenic determinants of comparatively low molecular weight is automatically avoided. Antibodies against low molecular weight immunogenic determinants grafted onto high particle weight bacterial particles can therefore be manufactured particularly readily with a very desirable high degree of specificity.

Whilst the invention offers the aforesaid special advantages with immunognnic materials having molecular weights below 150 000 and in particular below 100 000, it also offers substantial advantages if immunogenic materials of relatively high molecular weight such as gamma-globulins are coupled to bacterial particles. There as well substantially improved yields, specificities and avidities of antibodies were observed.

The cells involved in the immune response to naked bacteria and naked bacteria conjugates are macrophages, T-cells and B-cells. These cells are found together in organs and tissues involved in the immune response for example: the spleen, the lymph nodes throughout the body, the bone marrow, tonsils and adenoids, the wall of the small intestine and the skin.

The mechanism whereby naked bacteria are believed to work is two-fold, firstly with the co-operation of macrophages, T-cells and B-cells and that is called a T-cell dependent immune response and secondly with the co-operation of macrophages and B-cells and is called a T-cell independent immune response. In the first of these two mechanisms, naked bacteria conjugates would be engulfed by macrophages and decomposed to immuno-stimulant molecules and antigen containing molecules. The macrophage would then pass these immunogen-containing molecules to T-cells and these in turn would pass them to B-cells. The macrophages pass the immunostimulants to B-cells directly. Upon stimulation by the immuno-stimulants and antigen containing molecules the B-cells will proceed with the production of antibodies specific for the immunogen. The T-cells play the role of helping the B-cell to "decide" whether to produce antibodies or not.

In the second mechanism naked bacteria conjugates would be engulfed by macrophage and subsequently decomposed to immuno-stimulant molecules and immunogen containing molecules. Both of these are then passed directly to B-cells who in turn produce antibodies.

Our results to date confirm that both mechanisms are used for antibody production following naked bacteria conjugate administration.

The aforegoing should be contrasted against the far more limited mechanism by which LPS is effective as explained further above (see Background of the Invention).

The invention is not limited to the production of antibodies in living higher animals, but can also be applied to antibody production in tissue cultures or in bacterial cultures, more particularly in mono-clonal hybrid tissue or bacterial cultures. This may be done as follows in a manner known per se and therefore requiring no detailed description): according to one embodiment the immunogenic material according to the invention is used as aforesaid for immunising an animal, and cells of such animal which secrete antibodies are fused, e g. lymphocytes from the spleen of the immunised animal, with myeloma cells of a different animal, such hybrid cells then being cultured and cloned so that each clone produces large amounts of identical antibodies to a single immunogenic determinant.

The antibody production may be carried out in vitro (in cultures) throughout; or alternatively a sample of the clone ca be injected into animals. The relevant procedures are described by Cesar Milstein, Scientific American 243 (4), page 56 to 64.

DETAILED DESCRIPTION OF PREFERRED EMBODIMENTS

Example 1

Grafting of digoxin onto naked bacteria.

In order to introduce a reactive amine group into digoxin, the substance is first subjected t periodate oxidation and then reacted with hexamethylenediamine as follows: 109 mg of digoxin (0.14 milli mol) are suspended in 10 ml absolute ethanol at room temperature. 5 ml of 0.1M $NaIO_4$ are added dropwise with magnetic stirring. After 25 minutes 1.5 ml of 1M ethyleneglycol is added.

5 minutes later the reaction mixture is addeddropwise, with magnetic stirring to 2.44 g (0.02 mol) of hexamethylene diamine in 10 ml of water and of which the pH had previously been adjusted to 9.5 with 5% potassium carbonate. The pH is maintained in the 9.0 to 9.5 range by the dropwise addition of 5% potassium carbonate or 0.1M HCl respectively. After 45 minutes the pH is stable and 0.075 g of sodium borohydride, freshly dissolved in 5 ml water is added. 16 hours later the pH is lowered to 6.5 with 1 M formic acid. After 1 hour at pH 6.5 the pH is raised to 8.5 by the addition of 1M ammonia.

The reaction mixture is then dried with a rotary evaporator and the residue is taken up in a mixture of chloroform and ethanol (1:1) and purified on silica gel using a chloroform-ethanol mixture (3:2) as eluent. In this manner an amino group is introduced into the digoxin molecule after conjugation with hexamethylenediamine.

The naked bacteria are prepared as follows :

Salmonella Minn. R595 is cultured in an aqueous growth medium having the following composition per litre :

15 g peptone, 5 g yeast extract, 3 g NaCl, 2 g $Na_2HPO_4.12H_2O$, 0.2 g $MgSO_4.7H_2O$, 10 g glucose.

The bacteria are incubated for 7 days at 37° C.

Thereafter phenol is added (final concentration 1%) to kill the cells. The cells are separated off and washed repeatedly : first twice with distilled water, then twice with acetone and then once with ether followed by drying in vacuo. This product can be stored at room temperature until required.

For the hydrolysis in order to strip off O-antiqenic determinants. the dry bacteria are washed twice with 1% acetic acid and are then suspended in 1% acetic acid (1 g/ml) and heated to boiling for two hours.

The bacterial particles are separated and washed twice with distilled water followed by drying in vacuum. The dried powder constitutes the naked bacterial material.

The amine derivative of digoxin is then bonded covalently onto the naked bacteria as follows:

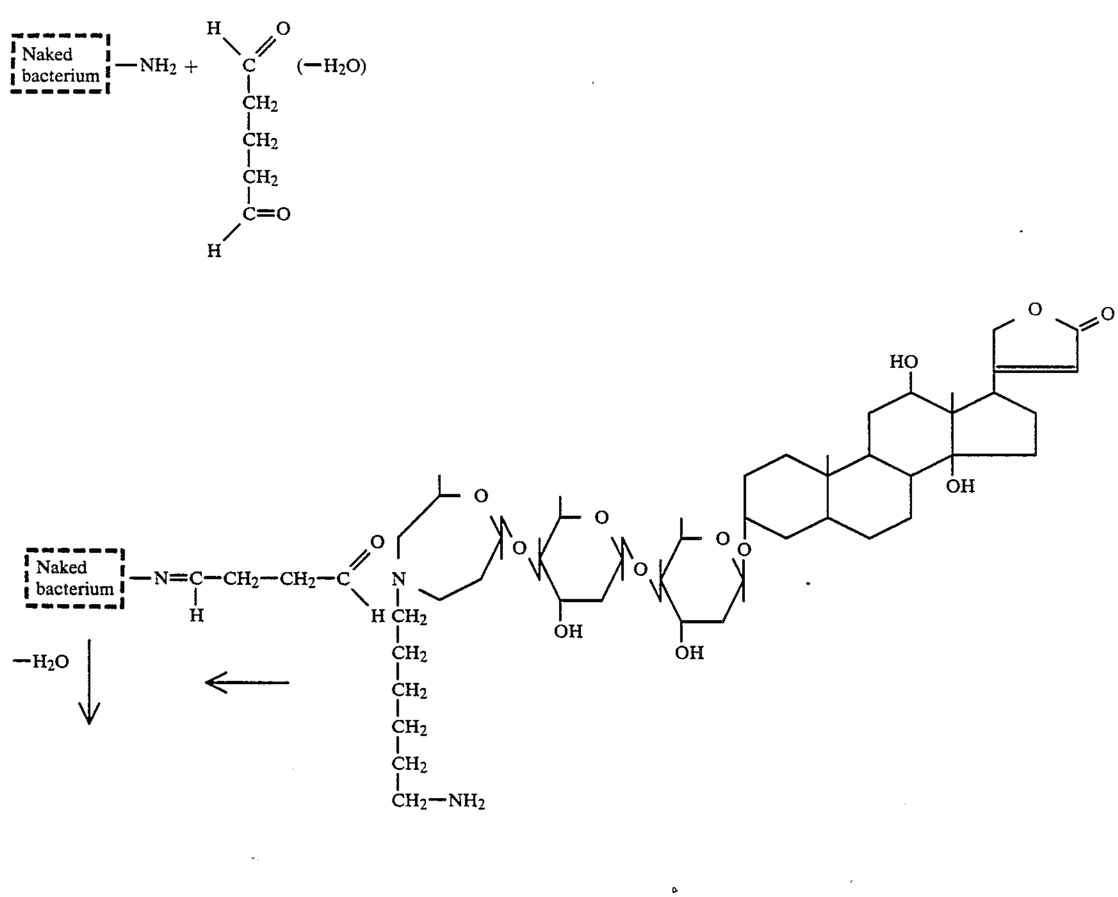

-continued

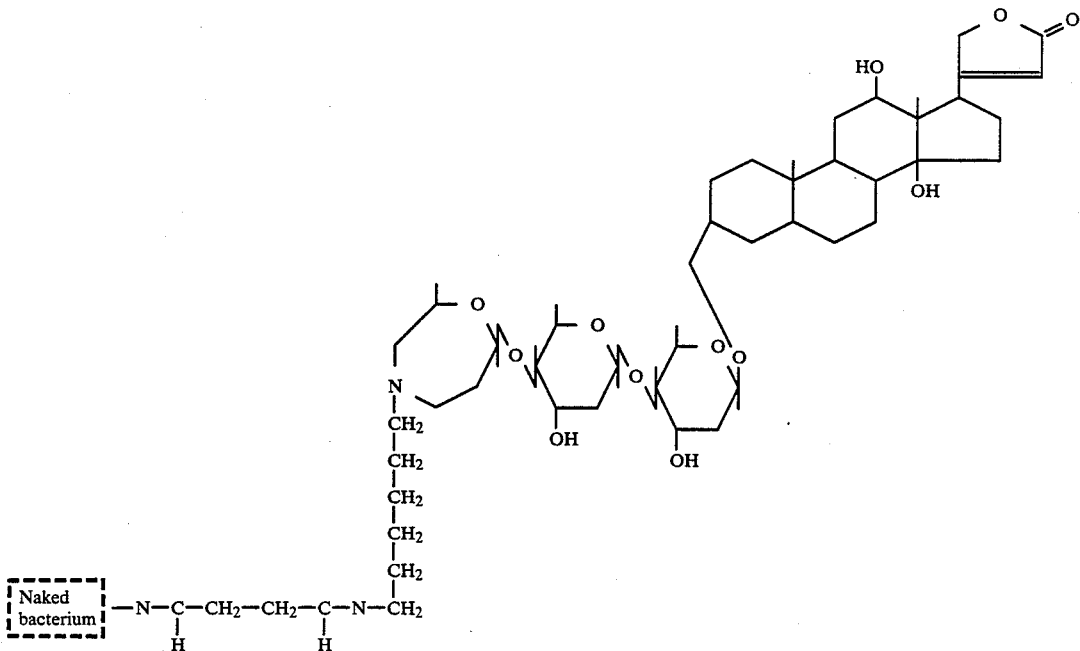

Digoxin naked bacterium conjugate 30 mg of the dried naked bacteria are reconstituted by being suspended in 6 ml water and incubated for 1 hr at 37° C. The supernatant is centrifuged off at 12 000 g. 6 ml 0.25% aqueous glutaraldehyde solution is added to the bacteria followed by 1 hour incubation at 37° C. in turn followed by centrifuging off the supernatant at 12000 g.

The reaction product is reacted for one hour at 37° C. derivative with 1 ml of a 1% solution of digoxin. in dimethyl sulphoxide (DMSO) or methanol, followed by centrifugation at 12000 g. The sediment is then reacted for 1 hour with 4.8 ml of 0.33% aqueous ethanolamine at 37° C. to block off the remaining aldehyde groups. The product is centrifuged at 12000 g and washed twice with 6 ml portions of water, each time followed by centrifugation at 12000 g. The product may then be suspended in 18 ml phosphate buffered saline solution (PBS) for use in immunisation.

EXAMPLE 2

Grafting of T3.(triiodothyronine) onto naked bacteria.

30 mg of naked bacteria are prepared as in Example 1 suspended in 6 ml of water and incubated for 1 hour at 37° C. to allow the bacteria to swell. The suspension is then centrifuged for 10 minutes at 12 000 g to remove the supernatant. 6 ml 0.25% glutaraldehyde aqueous solution is added followed by incubation for 1 hour at 37° C. Again the suspension is centrifuged for 15 minutes at 12 000 g to remove the supernatant.

1 ml of a 1% methanolic solution of the sodium salt of triodothyronine is added followed by incubation for one hour at 37° C. and centrifugation for 10 minutes at 12 000 g to remove the supernatant.

4.8 ml 0.33% ethanol amine solution is added followed 0 by incubation for one hour at 37° C. and centrifugation for 10 minutes at 12 000 g to remove the supernatant. The product is shaken up with 6 ml water and again centrifuged as before, followed by adding once again 6 ml of water and repetition of the centrifugation to remove the supernatant. The product is then taken up in 18 ml of phosphate buffered saline solution for immunisation.

EXMAPLE 3

Preparation of T4 (tetraiodothyronine) bonded to naked bacteria

The procedure is the same as in example 2 except that tetraiodothyronine is substituted for triiodothyronine.

EXMAPLE 4

Bonding of thyroxine onto naked bacteria.

The present example serves to illustrate the use of cyanogenbromide as a linkinq compound.

First the naked bacteria are "activated" with cyanogenbromide (CNBr) as follows :

2 mg of a 25 mg/ml solution of CNBr is placed in a suitable titration holder, magnetically stirred, and the pH is adjusted by means, of a pH-stat apparatus, using a 2 M sodium hydroxide solution for the adjustment of the pH to 11.5.

50 mg of naked bacteria are suspended in one ml water and allowed to swell for one hour at 37° C. The suspension then added to the abovementioned reaction mixture and the reaction is allowed to proceed for 6 minutes, during which time the pH is kept constant at 11.5. The naked bacteria are then washed on a sinter glass filter with water. These pretreated naked bacteria can now be stored at −10° C. until required for the next step.

The antigen is bonded to the activated naked bacteria as follows :

1 ml of 1% thyroxine solution is added suspension containing 30 mg of naked bacteria activated as described above. The mixture is incubated overnight and then centrifuged for 10 minutes at 12 000 g to remove the supernatant. The sediment is resuspended in 4.8 ml 0.5 M NaHCO solution and centrifuged. The supernatant is discarded. 4.8 ml of a 0.33% ethanol-amine solution is added. The mixture is left for one hour and then centrifuged. The supernatant is discarded. 6 ml 0.01 M HCl are added followed by centrifugation and discarding the supernatant. This step is repeated once with 6 ml 1 M NaCl and twice with 6 ml of water. The washed sediment is dried completely on a rotary evaporator and taken up in 18 ml phosphate buffed saline solution for immunisation.

Exactly the same procedure can be followed for coupling $T_3$ instead of $T_4$ to naked bacteria.

EXAMPLE 5

Immunisation of fowls with antigen bonded onto naked bacteria. (by POLSON's method)

The immunisation suspension prepared in accordance with one of the preceding examples is shaken up. To every 1 ml of suspension 1 ml of Freund's incomplete adjuvant is added and the mixture is shaken up till a stable emulsion is formed. This emulsion is injected into fowls at a dose of 1 ml per fowl, 0.5 ml being injected intramuscularly into each of the two breast muscles of the fowl. This corresponds to a dose of about 0.8 mg immunogen according to the invention. This immunisation is repeated twice a week for the first three weeks, after which periodic boosters are given. The first booster is given after one week and thereafter boosters are given monthly.

EXAMPLE 6

Production of fowl IgY

As from the 21st day after completion of the above (Example 5) immunisation, the eggs of the immunised fowls are collected. The eggs are broken and the egg yolk is carefully washed with water without breaking the yitelline memberanes The vitelline membrane are then broken and the egg yolks material is collected in a measuring flask. The volume is measured and polyethyleneglycol of molecular weight 6000 is added to a final concentration of 4 grams per 100 ml PEG. This causes precipitation of the ovalbumin, lipoproteins and casein-like proteins and the separation of lipids. These substances are removed by centrifugation followed by filtration of the supernatant through cottonwool resulting in a clear solution. The volume of the solution is again measured and more PEG is added to bring the total concentration of PEG to 12 g per 100 ml. This causes the precipitation of the antibodies which are removed by centrifugation and redissolved in 1/6 of the original volume of the egg yolk in phosphate buffer at pH 7.6, 0.1 M. The solution contains about 25 mg protein/ml.

The aforegoing is all done at neutral pH (6.5–7.8) for which reason it is preferred to use a dilute phosphate buffer (0.1M) as the aqueous medium throughout the process.

EXMAPLE 7

Immunisation of rabbits with naked bacteria bonded antigens

The naked bacteria suspensions are made up with Freund's incomplete adjuvant as described in Example 5. The rabbits are then inoculated with this emulsion by the administration of 2×0.5 ml doses injected at two different sites subcutaneously. This is repeated once a week for 8 weeks.

After the aforesaid inoculation regimen, only periodic boosters are given.

All injections are accompanied by a simultaneous intramuscular injection of the general antibiotic "Streptopen" (R) to guard against infection. After the first week 0,5 ml of 1:5 diluted adrenaline is injected subcutaneously 10 minutes prior to each inocculation as a precaution against anaphylactic shock.

Example 8

Antibodies against IgG

Rabbit immunoglobulin is bonded to naked bacteria with glutaraldehyde using the procedure described in Example 2, This carrier-bonded immunoglobulin is then used for the immunisation of leghorn hens as described in Example 5 and the antibodies are recovered as described in Example 6.

For purposes of comparison the immunisation and recovery of antibodies is repeated on similar leghorn hens using human IgG which had not been bonded to any carrier as the immunogen. The antibody yield as reflected in the agglutination titre for the naked bacteria bonded IgG was four dilution levels higher than for ordinary IgG.

EXAMPLE 9

Immunisation of sheep

The same procedure is followed as for rabbits in Example 7 except that the volumes injected are larger. 2 ml immunogen emulsion is injected each time, divided between two injection sites. The adrenaline and Streptopen injections are increased to 1 ml and 2 ml respectively.

Consistently high antibody titres are obtained and the antibodies have higher avidity than those raised by similar immunisation regimens using comparable conventional immunogens. Accordingly, the immunogens according to the invention are useful both as a means for commercial antibody production as well as vaccines for protective immunisation against patogens.

EXAMPLE 10

Isolation of IgG from blood

Blood is drawn from the jugular vein of sheep or from the main artery supplying the ear of rabbits. The blood is allowed to clot at room temperature (20° C.) for 3–5 hours and 25 is then centrifuged at 3000×g for 30 minutes. The clear serum obtained is diluted with 2 volumes of borate buffer (0,01 M, pH 8,6) and mixed carefully. Polyethylene glycol (PEG 6000) is added to a concentration of 15% m/v, followed by centrifugation at 12000×g for 10 minutes. The precipitate pellet is resuspended in the same volume of the borate buffer and the precipitation with PEG 6000 and centrifugation is repeated. The pellet is redissolved in a volume of phosphate buffer (0.1 M, pH 7.6) equal to half of the original serum volume.

EXAMPLE 11

Alpha-fetoprotein antibodies

Alpha-fetoprotein antibodies are commercially valuable because they are useful for large-scale screening of pregnant women (e.g. by RIA techniques) for spina bifida and anencephaly in the fetus.

Alpha-fetoprotein AFP), molecular weight 70 000 daltons, is synthesised first by embryonic yolk sack cells and later by fetal liver cells. It is the first alpha-globulin to appear and is the dominant seral protein of very early mammalian embryogenesis. During pregnancy some AFP is normally excreted into the amniotic fluids in the urine of the second trimestal fetus and is slowly removed by fetal swallowing. Much higher concentrations of AFP are found in the amniotic fluids of fetuses with open neural tube defects. As a result of movement of AFP across the placenta, the maternal serum AFP concentrations increase during pregnancy. Assays for AFP in maternal sera can therefore give an indication of these open neural tube defects of a fetus at an early stage during pregnancy.

There are large structural similarities between albumin and AFP. Any useful assays must be able to distinguish clearly between the two substances. In preliminary experiments attempts were made to immunise some fowls against albumin and some against AFP. The immungenic response was too small to produce useful concentrations of IgY against these immunogens in the egg yolks. Both substances were then coupled to naked bacteria by the procedure described in example 1. Hens are then immunised with the resulting immunogenic materials according to the procedure of Polson.

The hens are injected intravenously or intraperitoneally with naked bacteria conjugates resuspended in PBS, 50 μg of conjugate in 0.5 ml of PBS on day 1, 100 μg of conjugate in 0.5 ml of PBS on day 4. 200 μg of conjugate in 0.5 ml of PBS on day 7 and 200 μg of conjugate in 0.5 ml of PBS on day 11.

Eggs can be collected from day 14 but preferably from day 21 onwards.

In pilot tests conducted there were good avidities.

There was no cross reaction between the anti-AFP antibodies and albumin. There was a small degree of cross reaction of the anti-albumin antibodies with AFP. However, this is unimportant in the present context. It was found that the anti-AFP antibodies could be used to construct a precipitation RIA quite easily and that this RIA has the necessary sensitivity and repeatability.

EXAMPLE 12

Periodate oxidation of digoxin and coupling to naked bacteria 430 mg of digoxin (0.56 mM) are suspended in 20 ml absolute alcohol at room temperature. 20 ml of 0.1 M sodium metaperiodate is added dropwise with magnetic stirring.

After 25 minutes 0.6 ml of 1 M ethyleneglycol is added. 5 minutes later the reaction mixture is added dropwise with magnetic stirring to 600 mg of naked bacteria (see example 1) in 20 ml of water which had previously been adjusted to pH 9.5 with 0.4 ml of 5% potassium carbonate. The pH is maintained in the 9.0–9.5 range by the dropwise addition of 2 ml 5% potassium carbonate. After 45 minutes the pH is stable and 0.4 g sodium borohydride, freshly dissolved in 20 ml of water is added. 3 hours later 7.6 ml of 1 M formic acid is added to lower the pH to 6.5. After one further hour the pH is raised to 8.5 by the addition of 1.5 ml 1 M ammonia. The entire reaction mixture is then centrifuged for 10 minutes at 10 000×g and the supernatant is removed. The pellet is washed three times with phosphate buffered saline (PBS), whereafter 360 ml sterile PBS is added. The resulting suspension is then used for immunisation

EXAMPLE 13

Coupling of horseradish peroxidase to naked bacteria

Horseradish peroxidase is an enzyme containing a high percentage of carbohydrate which can be activated with cyanogenbromide and subsequently reacted with naked bacteria (which also have carbohydrate groups on their exterior surface) or vice versa.

2 ml of cyanogenbromide solution (25 mg/ml) is placed in a container and the pH of the solution is adjusted to 11.0 by the addition of 2 M NaOH solution. 50 mg horseradish peroxidase is dissolved in 2 ml water and added to the abovementioned solution. The pH is kept constant for 6 minutes whilst the reaction proceeds. The pH of the solution is then reduced to pH 7 by the addition of 0.1 M hydrochloric acid. The "activated" horseradish peroxidase is separated from contaminants by gel chromatography and is lyophilized.

5 mg of the lyophilisate is dissolved in 1 ml of phosphate buffer (pH 7.6, 0.1 M), 60 mg of naked bacteria are allowed to swell for one hour in 12 ml water after which the suspension is centrifuged at 10 000 g for 10 minutes. The sepernatant is removed and the pellet is resuspended in 5 ml 0.1 M of the phosphate buffer. The solution of activated horseradish peroxidas is then added to the naked bacteria suspension and allowed to react for 18 hours at 25° C. The suspension is centrifuged at 10 000×g for 0 minutes, the supernatant is removed and the pellet is washed 3 times with PBS. The pellet is finally resuspended in 36 ml of sterile PBS for immunisation.

The resulting antibodies are intended for use in ELISA.

EXMAPLE 14

Reaction of carboxvl qroups with amine groups. $T_3$ (see example 2) can also be grafted to naked bacteria via its carboxyl groups and via the amine groups on the surface of the naked bacteria. ($T_3$ is merely used as a convenient example). 60 mg of naked bacteria are suspended in 25 ml of water and 30 mg of 1-cyclohexyl-3-(2-morpholinyl-4-ethyl) carbodiamide metho-p-toluenesulphonate (morpho-CDI) is added. 20 mg of $T_3$ in its free acid form, dissolved in 5 ml of dimethylformamide is then added dropwise whilst stirring. The pH is kept constant at 5.5 with dilute hydrochloric acid or sodium hydroxide. After 10 minutes an additional 10 mg of carbodiamide is added. The suspension is kept at room temperature with constant stirring in the dark for 18 hours. The suspension is then centrifuged at 10 000 g for 10 minutes, the supernatant is removed and the pellet is washed three times in PBS. The final pellet is.resuspended in 36 ml of sterile PBS for use in immunisations.

EXAMPLE 15

Reactions of carboxyl groups with hydroxyl groups

This example serves to illustrate a case where the amine groups on naked bacteria are first succimilated so as to form carboxyl groups on the surface of the naked bacteria and serve as a reactive intermediate, e.g. for the coupling of beta-ecdysone (for reaction scheme see further above). 60 mg of naked bacteria are suspended in 2 ml of dry dimethylsulphoxide (DMSO). Succinic anhydride (210 mg) is added in small increments to this suspension. The reaction is allowed to proceed for 38 minutes, whereafter 10 ml of water is added. The suspension is centrifuged and the supernatant is removed.

The pellet is resuspended in 10 ml of water centrifuged and the supernatant is removed This washing step is repeated twice. The resulting pellet is lyophilised for further use in the next step.

The pellet (60 mg) prepared as described above is suspended in 15 ml of dry DMSO. To this suspension 30 mg beta-ecdysone, 4-dimethyl amino pyridine (1 mg) and 1-ethyl-3-(3-dimethyl- aminopropyl)-carbodiimide hydrochloride (422 mg) is added.

The mixture is magnetically stirred for 4½ hours. 15 ml of distilled water is then added and the resulting suspension is centrifuged at 10 000 x g for 10 minutes. The supernatant is removed and the pellet resuspended in 20 ml of distilled water. This suspension is centrifuged and the supernatant again removed. The washing process is repeated twice, whereafter the naked bacteria conjugate is resuspended in 36 ml df sterile PBS for use in an immunisation.

EXAMPLE 16

Reaction of activated carboxyl groups with primary amines

This example illustrates how activated carboxyl groups are formed by means of the esterification of carboxyl groups with N-hydroxysuccinimide.

The N-hydroxysuccinimidyl of ester of testosterone-3-(0carboxymethyl) oxide is synthesised as described by Tantchou et alia (J. of Immunoassay, 1(1), 129–147 (1980)) on page 133. This substance is then reacted with naked bacteria as follows : 60 mg naked bacteria are swollen in 12 ml of distilled water for one hour. 0.06 mg N-hydroxysuccinimidyl ester of testosterone are dissolved in 0.2 ml methanol. The naked bacteria suspension is centrifuged for 10 minutes at 10 000×g. The supernatant is removed and the pellet is resuspended in 1 ml of water., To this suspension add the solution of N-hydroxysuccinimidyl ester to proceed of testosterone. The reaction is allowed-for 2 hours at 4° C. Add 10 ml of cold (4° C.) distilled water to the suspension. Centrifuge at 10 000×g for 10 minutes and remove supernatant. Add 10 ml of PBS, resuspend pellet and centrifuge at 10 000×g for 10 minutes. Repeat this washing step and resuspend the pellet in 36 ml of sterile PBS for immunisation purposes.

EXAMPLE 17

Reaction of anhvdrides with primary amines

Anhydrides react with primary amines forming amide bonds and resulting in the effective production of carboxyl groups in the place of amine groups.

Take 1 g of metoclopramide and dissolve in 5 ml dry chloroform. Dissolve 0.346 g of succinic anhydride in 2 ml dry chloroform. Carefully add the succinic anhydride solution to the solution of metoclopramide and reflux for 4 hours. Remove the chloroform and recrystallise from ethylacetate to which a small proportion of petroleum ether has been added. Approximately 1 g of succinilated metoclopramide is formed. This is an example of succinilated derivatives of a large variety of substances which can be esterified with N-hydroxysuccinimide by means of DCC according to the method of Rudinger and Ruegg (Biochem. J. 133 538, (1973). The resulting activated carboxylic acid derivatives are reacted with naked bacteria as described for the production of naked bacteria conjugates in the preceding examples.

EXAMPLE 18

Maleimide derivates of antigens

Maleimide groups are introduced into antigens by means of the bifunctional reagent N-hydroxy succinimide ester of N-(-4-carboxy-cyclohexylmethyl) maleimide (Eur. J. Biochem. 101, 395, (1979).

Take 70 mg of albumin (bovine serum albumin) and dissolve in 15 ml phosphate buffer (0.1 M, pH 7.0). 1.5 mg of N-hydroxysuccinimide ester of N-(4 carboxycyclohexylmethyl) maleimide is dissolved in 0.1 ml dioxane and added dropwise whilst stirring to the albumin solution. The reaction mixture is incubated at 30 ° C. for 4 hours after which the reactive intermediate is isolated on "Sephadex G 25" using 0.1 M phosphate buffer, pH 7.0 by means of gel filtration chromatography.

This maleimide derivative is then coupled to naked bacteria via naturally occurring or chemically introduced SH-groups. If desired, additional -SH groups can be introduced via the method of Klokj and Heiney (Archives of Biochem. and Biophysics 96, 605,(1962)).

60 mg of naked bacteria containing SH groups are suspended in 5 ml 0.1 M phosphate buffer pH 7.0. A solution of 5 mg of the above described maleimide derivative of albumin is dissolved in 0.5 ml 0.1 M phosphate buffer, pH 7.0 and is added to the naked bacteria suspension. The reaction mixture is incubated for 20 hours at 4° C. under an atmosphere of nitrogen. The naked bacteria are then isolated by centrifugation and the pellet is washed 3 times with 0.1 M phosphate buffer, pH 7.0 whereupon the pellet is suspended in 36 ml of sterile PBS for immunisation.

EXAMPLE 19

Modification of example 18

The method according to example 18 is modified as follows in that first the maleimide derivative of naked bacteria is made and then a substance containing a thiol group is reacted with the derivative.

Take 60 mg of naked bacteria and swell for one hour in 0.1 M phosphate buffer, pH 7.0. 1.5 mg of N-hydroxysuccinimide ester of N-(4)-carboxy-cyclohexylmethyl) maleimide is dissolved in 0.1 ml dioxane and added dropwise whilst stirring to the naked bacteria suspension. The reaction is allowed to proceed for 4 hours at 30° C. after which the reactive intermediate is isolated by centrifugation and washed 3 times with phosphate buffer. The pellet is finally resuspended in 5 ml 0.1 M phosphate buffer, pH 7.0. 5 mg of insulin (an example of a protein containing SH groups, is dissolved in 0.5 ml, 0.1 M phosphate buffer pH 7.0 and allowed to react with the naked bacteria intermediate for 20 hours under an atmosphere of nitrogen. Finally, the insulin-naked bacteria conjugate is isolated by centrifugation and washed 3 times in 0.1 M phosphate buffer, pH 7.0. The pellet is finally suspended in sterile PBS (36 ml) for use in immunisation.

EXAMPLE 20

Coupling via disulphide exchange

In this method the antigen as well as the naked bacteria are first modified for coupling.

The reaction takes place in 3 steps:
1. Introductibn of 3-(2-pyridyl dithio) propionyl (PDT) groups into antigens (e.g. proteins) by N-succinimidyl 3-(2)-pyridyldithio) propionate (PDP) as follows: bovine serum albumin (BSA) is used as the antigen. 80 mg thereof is dissolved in 2 ml of water and 0.3 ml of 20 mM PDP solution in absolute ethanol is added. The two reagents are mixed and allowed to react for 30 minutes at 25° C. after which excess SPDP reagent is removed by dialysis against PBS for 72 hours at 4° C. This results in the formation of a BSA-PDT conjugate.

2. Coupling of dithiodiglycolic acid (DTDG) to naked bacteria by means of 1-ethyl-3-(3-dimethyl-aminopropyl) carbodiimide (EDCI):

182 mg DTDG is dissolved in 1 ml 2 M NaOH. The solution is then diluted to 25 ml by adding borate buffered saline (pH 6). 1 ml of a suspension of naked bacteria (60 mg) in borate buffered saline (pH 7) is added. After thorough mixing a freshly prepared solution containing 250 mg of EDCI in 2.5 ml water is added with mixing. The suspension is left at room temperature for 30 minutes with occasional swirling. The naked bacteria conjugates are then removed by centrifugation and washed three times with PBS. They are stored in 2 ml PBS at 4° C. until used.

3. The previously prepared DTDG-naked bacteria conjugate is then reduced to thioglycolyl naked bacteria with the aid of dithiothreitol (DTT):

The 2 ml DTGG-naked bacteria suspension is brought to room temperature and 1 ml of 1 M DTT is added and mixed. The reaction is allowed to continue for one hour with magnetic stirring. The naked bacteria are then removed by centrifugation and washed four times with PBS and finally suspended in 2 ml PBS for coupling to DSA-PDTP.

4. Coupling of PDT -DSA to thioglycolyl-naked bacteria. 2 mg PDTP-BSA dissolved in PBS (200 µl) is mixed with 2 ml of thioglycolyl-naked bacteria suspension previously prepared and allowed to react overnight with slow magnetic stirring. The resulting naked bacteria conjugate is removed by centrifugation, washed 3 times with PBS and finally resuspended in 36 ml of sterile PBS for immunisation.

EXAMPLE 21

Toxins coupled to naked bacteria

Cholera toxin is coupled to naked bacteria as described in example 2 modified in that 10 mg of cholera toxin in 1 ml PBS is substituted for the 1 ml of 1% methanolic $T_3$ solution.

This procedure can also be employed for preparing conjugates of snake venom.

EXAMPLE 22

Carrier bound testosterone 60 mg naked bacteria are swollen in lU ml distilled water for 1 hour as in previous examples.

The iodohistamine ester of testosterone hemi-succinate is prepared as,described by Tantchou and Slaunwhite in J. of Immunoassay, 1(1), 129–147 (1986), asdescribed there on page 139 under the heading "Reaction of iodohistamine with activated esters". 5 mg of the ester are dissolved in the minimum volume of water, added to the naked bacteria suspension and mixed well. The suspension is exposed to ultraviolet light (wave length 211 nm—mercury lamp) for 5 minutes. After irradiation the suspension is centrifuged at 10 000 ×g for 10 minutes. The supernatant is removed, the pellets are washed three times with 20 ml PBS and the final pellet is dissolved in 36 ml sterile PBS for use in immunisation.

EXAMPLE 23

Diesters of dicarooxylic acids as linking reagent

A solution is prepared of 2 - 20 mg/ml of the diester of glutaric acid (or pimelic acid) prepared by condensation of N-hydroxysuccinimide using dicyclohexyl carbodiimide (J. Am. Chem. Soc. 86,1839–1842, (1964)). 60 mg of naked bacteria are swollen for 1 hour in 0.1 M phosphate buffer pH 7.0. The above solution (containing 1.5 mg) of the diester is added to the naked bacteria with stirring.

The reaction is allowed to proceed for 6 hours at room temperature. IgY (5 mg) dissolved in 0.5 ml phosphate buffer (0.1 M, pH 7.0) is added and allowed to react overnight. Unreacted reactive groups can optionally be blocked with mercapto ethylamine or ethanolamine.

The naked bacteria conjugate is recovered and washed and resuspended as in the previous examples. In this example glutaric and pimelic acid diesters of N-hydroxysuccinimide react with amine groups on protein molecules with the liberation of N-hydroxysuccinimide.

EXAMPLE 24

Bismaleimides as crosslinking agents

Example 23 is modified by using as the bifunctional crosslinking reagent a bismaleimide of the structural formula

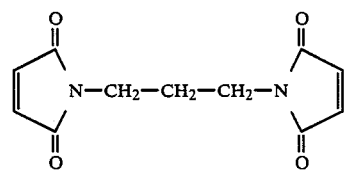

This reagent is prepared according to the method of Goodfriend et alia (Science, 144, 1344–1346 (1964)). As for the remainder the procedure is the same.

The bismaleimides react with sulphydryl groups of proteins and similar molecules by adding onto the double bonds of the maleimide rings.

EXAMPLE 25

Example 23 is modified by using as the bifunctional crosslinking reagent the N-hydroxysuccinimide ester of N-(4)-carboxycyclohexylmethyl)-maleimide.

The reactions occurring in that case are a combination of the reactions involved in example 23 and 24.

EXAMPLE 26

Example 23 is modified by using as the bifunctional crosslinking reagent, the N-hydroxysuccinimide ester of 3(2-pyridyl-dithio)-propionic acid of the formula

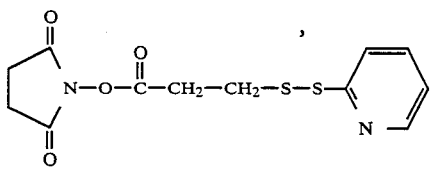

In this example amine groups of protein or the like react with the one end of the cross-linking agent with the elimination of N-hydroxysuccinimide whilst the other end reacts with sulphydryl groups by way of disulphide exchange with the elimination of 2-mercapto-pyridine.

Blocking of unreacted functional groups can once again be carried out with mercapto ethylamine.

Example 27

The immune response of 3 month old rabbits was measured by hemolysis. Maximum response achieved after immunization of:

|   | | 1st Immunization | Booster | Day 51 |
|---|---|---|---|---|
| 1. | 100 μg Conjugate containing 1,25 μg TNP/mg bacteria. | $(1:2^{3.67})1:13$ | $(1:2^{0.33})$ | 1:1.25 |
| 2. | 100 μg Conjugate containing 5 μg TNP/mg bacteria. | $(1:2^{7.67})1:204$ | $(1:2^9)$ | 1:512 |
| 3. | 100 μg Conjugate containing 15 μg TNP/mg bacteria. | $(1:2^{10.67})1:1629$ | $(1:2^{11.33})$ | 1:2574 |
| 4. | 10 μg Conjugate containing 5 μg TNP/mg bacteria. | $(1:2^{5.33})1:40$ | $(1:2^{5.33})$ | 1:40 |
| 5. | 10 μg Conjugate containing 15 μg TNP/mg bacteria. | $(1:2^{7.33})1:160$ | $(1:2^{10.33})$ | 1:1287 |
| 6. | 1 μg Conjugate containing 5 μg TNP/mg bacteria. | $(1:2^3)1:8$ | $(1:2^1)$ | 1:2 |
| 7. | 1 μg Conjugate containing 15 μg TNP/mg bacteria. | $(1:2^{4.67})1:25$ | $(1:2^{3.67})$ | 1:13 |

Conclusions:
(a) 1, 4, 6, 7 induced an initial immune response but retained no immune memory over 51 days i.e. showed no increased response after the booster.
(b) 2, 3, 5 induced a high initial response and retained immune memory as is shown by the increased secondary immune response.
(c) 2 and 3 show that although the conjugate administered contains only 3 times the amount of the TNP the immune response achieved is 1629/204 i.e. 8 times higher.
(d) 2 and 5 show that comparable immune responses can be achieved using 100 μg of 5 μg TNP/mg bacteria i.e. 500 ng of TNP and 10 μg of 15 μg TNP/mg bacteria i.e. 150 ng of TNP. This means that a higher loading of antigen (TNP in this case) per unit mass of bacteria will allow a saving of antigen.

EXAMPLE 28

Immunisation of rabbits with naked bacteria bonded immunogens was carried out via the intravenous route. The naked bacteria conjugates are resuspended in PSS. Rabbits are inoculated intravenousy with 50 μg of conjucate in 0.5 ml of PBS on day 1, 100 μg of conjucate in 0.5 ml of PBS on day 4,200 μg of conjucate in 0.5 ml of PBS on day 7 and 200 μg of conjugate In 0.5 ml of PSS on day 11. Blood can be drawn on day 18 for hIgh titre antisera. This procedure can be followed also for sheep mice and baboons.

EXAMPLE 29

Reduced cross-activities achieved using naked bacteria as carriers compared to BSA.

Rabblts were immunized with testosterone-3-carboxy-methyl-oxlme-BSA in PBS esulsified in Freunds adjuvant and immunised subcutaneously as is standard practIce. A second qroup of rabbits was immunized with testosterone-3-carboxy-methyl-oxime naked bacteria via the ntravenous route. All antisera in both groups gave a good binding to testosterone. Cross-reactivities with 5-dihydrotestosterone showed the following results.

| Immunogen | Average percentage cross-reactivity with 5-α-DHT |
|---|---|
| T-3-CMO-BSA | 76.7 |
| T-3-CMO-NB | 26.1 |

From this result it can clearly be seen that naked bacterial used as carriers result in antibodies with lower cross-reactivities.

EXAMPLE 30

Increased avidities achieved using naked bacteria as carriers compared to BSA.

The rabbits used in the cross-reactivity experiment were also analyzed for anti body avidity. The following results were achieved.

| Immunogen | Average affinity constant, K in liters/mole × $10^{10}$ |
|---|---|
| T-3-CMO-BSA | 0.296 |
| T-3-CMO-NB | 2.965 |

This result indicates that the affinity constant of NB induced antibodies is 10 times higher than antibodies induced to BSA carrer bound testosterone.

The above indicates a verv high aviditvy.

EXAMPLE 31

The use of naked bacterla !n the preparation of monoclonal antibodies. Balb/c mice were lmsunlzed with a testosterone-17β-hemlsucclnatenaked bacteria conjugate in Freunds incomplete adjuvant subcutaneously and intraperitoneally until high anti-testosterone antibody titers were achieved. The mice were then sacrificed their spleens removed and hydrodomas produced according to the procedure of Milstein and Köhler. The monocional antibodies produced were selected for suitability and the clone NT17-7D1/F8 was used to produce monocional antibodies. This monocional antibody had an affinity constant of $6.9 \times 10^8$ liters/mole and a titer of 1:225 000 as tested by radioimmunoassay.

Example 32

Preactivaiton of naked bacterial.—manufacture of carrier substance (a) By means of glutaraldehyde: (as in example 2) 30 mg of naked bacteria are suspended in 6 ml of water and incubated for 1 hour at 37° C. to allow the bacterial to swell. The suspension is then centrifuged for 10 minutes at 12 000 g and the supernatant removed. 6 ml 0.25% glutaraldehyde aqueous solution is added followed by incubation for 1 h at 37° C. the suspension is then centrifuged for 15 minutes at 120000 g and the supernatant removed. The pellet is then washed 3 times with 6 ml of water by successive centrifugation and resuspension steps. Finally the pellet is lyophilized. Storage: Preactived bacteria of this type should be stored dessicated at 4° C. The have a shelf life of approximately 6 months.

(b) By means of CNBr (as in example 4)

2 ml of 25 mg/ml solution of CNBr is placed in suitable titration holder, magnetically stirred, and the pH is adjusted by meand of pH-stat apparatus, using a 2 M sodium hydroxide solution for the adjustment of the pH to 11.5.

50 mg of naked bacteria are suspended in one ml water and allowed to swell for one hour at 37° C. The suspension is then added to the abovementioned reaction mixture and the reaction is allowed to proceed for 6 minutes, during which time the pH is kept constant at 11.5. The naked bacteria are then washed on a sinter glass filter with water.

The pellet is then lyophlllized.

Storage: Dessicated at 4° C. Shelf-life approximately 3 months.

(b) By means of the N-hydroxy-succinimide ester of N--(4-carboxy-cyclohexylmethyl) -malemide (as in example 19).

Take 60 mg of naked bacteria and swell for one hour in 0.1 M phosphate buffer, pH 7.0. 1.5 mg of N-hydroxy-succinimide ester of N-(4)-carboxy-cyclohexylmethyl)-maleimide is dissolved in 0.1 ml dioxane and added dropwise whilst stirring to the naked bacteria suspension the reaction is allowed to proceed for 4 hours at 30° C. after which the reactive intermediate is isolated by centrifugation and washed 3 times with phosphate buffer.

The pellet is then washed 3 times with 5 ml portion of water and lyophilized. Storage: Dessicated at 4° C. Shelf life approximately 6 months.

(d) Preactivation by the introduction of 3-(2-pyridyl dithio) propionyl (PDT) groups by means of N-succinimidyl-3-(2)-pyridyldithio) propionate (SPDP) (as in example 20) 60 mg of naked bacteria are suspended in 5 ml of water and 1 ml of 20 mM SPDP are added. This mixture is allowed to react for 30 minutes at 25° C. with intermittent mixing. Excess SPDP is removed by centrifugation and subsequent washing with 10 ml portions of water. The pellet is finally lyophilized.

Storage: Dessicated at 4° C. Shelf-life approximately 6 months.

(e) Preactivation by means of diesters of dicarboxylic ester (as in example 23).

A solution is prepared of 2 - 20 mg/ml of the diester of glutaric acid (or pimelic acid) prepared by condensation of N-hydroxysuccinimide using dicyclohexyl carbodiimide (J. Am. Chem. Soc. 86, 1839–1842 (1964)). 60 mg of naked bacteria are swollen for 1 hour in 0.1 M phosphate buffer pH 7.0. The above solution (containing 1.5 mg) of the diester is added to the naked bacteria with stirring.

The reaction is allowed to proceed for 6 hours at room temperature.

The excess diester is removed by centugation and removal of the supernatant. The pellet is finally washed 3 times with 10 ml aliquots of water and lyophilized. Storage: Dessicated at 4° C. Shelf-life approximately 3 months.

EXAMPLE 33

Comparison of "naked" bacteria from different species:

Naked bacteria were prepared from S-minnesota R595, E.coli EH 100. S.abortus equi. Amounts of natural antgenic determinants still remaining on naked bacteria.

The portions that are stripped from *S. minnesota* R595 consist solely of KDO. A KDO determination can therefore be used to determine the amounts still remaining on the bacterial surface. Similarly *E. coli* EH 100, an Ra type mutant, posesses KDO in its natural antigenic determinants and the KDO determination can also be used to determine remaining antigenic determinants. If naked bacteria are manufactured from *Salmonella abortus equi*, an S-form bacterium, and an abequose determination can be used to determine the amounts of natural antigenic determinants still remaining on the bacterial surface.

To determine the amounts of natural antigenic determinants i.e. KDO in the case of *S. minnesota* R555 and *E. coli* EH100 and abequose in the case of *S, abortus equi,* 200 mg of each of these bacteria were suspended in 2 ml of 2% acetic acid and incubated at 100° C. for 2 hours. KDO and abequose determinations were then performed on the supernatants. The results were as follows:

| | |
|---|---|
| *S. minnesota* R595 | Amount of KDO released = 0.812 mg = 0.406% |
| *E. coli* EH 100 | :Amount of KDO released = 0.406 mg = 0.203% |

*Salmonella abortus* equi: Amount of abequose released=6.83 mg=3.415%.

The amounts of sugars are those naturally occurring in the antigenic determinants. In order to determine the amounts still remaining on naked bacteria the follwing procedure was followed. Naked bacteria were prepared from *S. minnesota* R595, *E. coli EH* 100 and *S. abortus* equi by treatment of these bacteria with 7% acetic acid for 1 hour at 100° C. (Standard procedure). The naked bacteria thus obtained washed with water and dried in the usual manner. 200 mg portions of each of these different naked bacteria types were then taken and suspended in 2% acetic acid and incubated for 2 hours at 100° C. to release all the sugars that might still have remained after stripping. KDO and abequose determinations were then performed on the supernatants.

The results were as follows;

*S. minnesota* R595

Amount of residual *KD*0 released = 0.0166 mg = 0.0083%

*E. coli* EH 100

Amount of residual *KD*0 released = 0.02275 mg = 0.011375%

*S. abortus* equi

Amount of residual abequose released = 0.4871 mg = 0.24355%

This effectively means that the following percentages of natural antigenic determinants still remains on the bacterial i.e. *S. minnesota R*595..

$$\frac{0.0166}{0.812} \times \frac{100}{1} = 2.04\%$$

*E.* coli *EH* 100

$$\frac{0.02275}{0.406} \times \frac{100}{1} = 5.6\%$$

*S. abortus* equi

-continued $$\frac{0.4871}{6.83} \times \frac{100}{1} = 7.1\%$$

It can be seen that although the efficiency of cleaving determinants off the bacterial surface increases with less natural antigenic determinant present on the bacterial surface, the procedure is quite generally applicable to produce carrier substance denuded e.g. of at least 80% of the natural determinants. In the above example the removal was approximately 93–98% complete.

The aforegoing examples, when read with the teachings contained in the description of the invention preceding the examples will enable the person skilled in the art to practise all aspects of the invention as defined in the following claims, which themselves constitute part of the present disclosure.

What we claim is:

1. A carrier substance for immunogenic determinants, comprising immunogenicity-increasing carrier particles derived from gram-negative bacterial cells substantially devoid or depleted of natural immunogenic determinants of the cells and comprising that region of the cells which includes lipid A and from there ranges inwardly towards the cell interior and including cell wall material, the particles having been chemically treated with a linking reagent in an amount to provide covalently bonded intermediate linking moieties exposed on the particles, providing reactive functional groups adapted to be bonded covalently to an immunogenically effective amount of selected haptens or immunogens comprising immunogenic determinants, while preserving the adjuvant character of the lipid A and cell wall material.

2. A carrier substance as claimed rn claim 1, wherein the particles are gram-negative bacterial cell particles subjected to chemical cleavage to substantially free the lipid A of 0-determinant-carrying material external of the lipid A, followed by covalent bonding to the particle exterior of the intermediate linking moieties.

3. A carrier substance as claimed in claim 2, wherein the cell walls of the cell particles are substantially intact.

4. A carrier substance as claimed in claim 2, wherein 80% or more of the natural O-antigens have been cleaved off.

5. A carrier substance as claimed in claim 4, wherein 90% or more of the natural O-antigens have been cleaved off.

6. A carrier substance as claimed in claim 5, wherein from 92 to 98% of the natural 0-antigens have been cleaved off.

7. A carrier substance as claimed in claim 1, wherein the linking reagent with which the particles have been treated is a bifunctional linking agent comprising two functional groups.

8. A carrier substance as claimed in claim 7, wherein the two functional groups of the bifunctional linking agent are the same.

9. A carrier substance as claimed in claim 7, wherein the two functional groups of the bifunctional linking agent are different.

10. A carrier substance as claimed in claim 7, wherein the functional groups are selected from the group consisting of aldehyde, imide, amino, cyano, halogen, activated carboxyl, carboxylic acid anhydride or a maleimide.

11. A carrier substance as claimed in claim 10, wherein the linking agent is a dialdehyde, diamine, cyanogen bromide, N-succinimidyl-3(N-succinimidyl)-propionate, or a N-hydroxyorsuccimide ester of N-(-4-4-carboxy-cyclohexyl) maleimide.

12. A carrier substance as claimed in claim 1, wherein the linking moieties are present in an amount adapted to bond hapten or immunogen in excess of 1–2 μg/mg of particles on a dry mass basis.

13. A carrier substance as claimed in claim 12, so adapted to bond from 1 to about 200 μg hapten or immunogen per mg of particles on a dry mass basis.

14. A carrier substance as claimed in claim 1 which has been converted into an immunogenic substance in that the reactive functional groups have been reacted to covalently bond selected haptens or immunogens comprising immunogenic determinants for a desired immune response by antibodyproducing cells.

15. A carrier substance converted into an immunogenic substance according to claim 14 in the form of an injectable vaccine.

16. A carrier substance according to claim 14 to which has been covalently bonded hapten or immunogen in excess of 1–2 μg/mg of particles on a dry mass basis.

17. A carrier substance according to claim 14 to which has been covalently bonded from 1 to about 200 μg hapten or immunogen per mg of particles on a dry mass basis.

18. A carrier substance according to claim 14 to which has been covalently bonded 5–50 μg hapten or immunogen per mg of particles on a dry mass basis.

19. An immunogenic substance with inherent adjuvant properties, comprising carrier particles having an exterior surface, derived from gram-negative bacterial cells having a membrane including an outer periphery known as the cell wall and lipid A, which particles include the cell region ranging inwardly from lipid A to the membrane, both inclusive and from which particles any cell material beyond lipid A, including O-antigen has been removed by chemical cleavage whollyor predominantly and further comprising an immunogenic determinant for producing a desired immunogenic response in living, antibody-producing cells, the determinant being coalently bonded by a synthetic linking reaction to the exterior surface of the carrier particles in a form permitting immuno-recognition by antibody-producing cells, the immunogenic determinant containing immunogenic information which elicits a desired response and the adjuvant character of the particles being preserved.

20. A substance as claimed in claim 19, wherein 80% or more of the natural O-antigens have been cleaved off the particles.

21. A substance as claimed in claim 20, wherein 90% or more of the natural 0-antigens have been cleaved off.

22. A substance as claimed in claim 21, wherein from 92 to 98% of the natural, 0-antigens have been cleaved off.

23. An immunogenic substance according to claim 19, wherein the immunogenic determinant is bonded directly to the carrier bacterial particle.

24. An immunogenic substance according to claim 19, wherein the immunogenic determinant is bonded to the carrier bacterial particle via a bifunctional linking agent.

25. A substance as claimed in claim 24, wherein the two functional groups of the bifunctional linking agent are the same.

26. A substance as claimed in claim 24, wherein the two functional groups of the bifunctional linking agent are different.

27. A substance as claimed in claim 24, wherein the functional groups are selected from the group consisting of aldehyde, imide, amino, cyano, halogen, activated carboxyl, carboxylic acid anhydride or a maleimide.

28. A substance as claimed in claim 27, wherein the linking agent is a dialdehyde, diamine, cyanogen bromide, N- succinimidyl-3(N-succinimidyl)propionate, or a N-hydroxysuccinimide ester of N-(-4-4-carboxycyclohexyl)maleimide.

29. A substance as claimed in claim 19, wherein the cell walls of the cell particles are substantially intact.

30. A substance as claimed in claim 19, wherein the immunogenic determinant is foreign to the carrier bacterial particle.

31. A substance as claimed in claim 30, wherein the immunogeni determinant is an antibody.

32. A substance as claimed in claim 19, wherein the immunogenic determinant is provided by a hapten or antigen covalently bonded to the carrier particles in an amount in excess of 1-2 $\mu$g/mg of particles on a dry mass basis.

33. A substance as claimed in claim 32, comprising from 1 to about 200 $\mu$g hapten or immunogen per mg of particles on a dry mass basis.

34. A substance as claimed in claim 33, comprising 5-50 $\mu$g hapten or immunogen per mg of particles on a dry mass basis.

35. A substance as claimed in claim 34, comprising 5-20 $\mu$g hapten or immunogen per mg of particles on a dry mass basis.

36. A substance as claimed in claim 19, wherein the immunogenic determinant has a molecular weight of less than 150,000 Daltons.

37. A substance as claimed in claim 36, wherein the molecular weight is less than 100,000 Daltons.

38. A substance as claimed in claim 37, wherein the molecular weight is less than 30,000 Daltons.

39. A substance as claimed in claim 19 in the form of an immunogenic composition which elicits an immunogenic response for active protective immunisation against a disease or pathological condition, and which comprises an immunogeni determinant containing immunogenic information for producing the desired specific immunogenic response covalently bonded to the carrier particles.

40. In a method of raising antibodies against an immunogenic determinant which comprises challenging antibody-producing living cells with an immunogenic determinant, the improvement which comprises so challenging the cells with an immunogenic substance with inherent adjuvant properties, comprising immunogenicity-increasing carrier particles having an exterior surface, derived from gram-negative bacterial cells having a membrane including an outer periphery known as the cell wall and lipid A, which particles include the cell region ranging inwardly from lipid A to the membrane, both inclusive and from which particles any cell material beyond lipid A, including O-antigen has been removed by chemical cleavage wholly or predominantly and further comprising an immunogenic determinant for producing a desired immunogenic response in living, antibody-producing cells, the determinant being covalently bonded by a synthetic linking reaction to the exterior surface of the carrier particles in a form permitting immuno recognition by antibody-producing cells, the immunogenic determinant containing immunogenic information which elicits a desired response.

41. A method according to claim 40, which further comprises concentrating and recovering the antibodies raised.

42. A method according to claim 41, wherein the antibodies are incorporated in a composition for use as an anti-serum.

43. A method according to claim 41, wherein the antibodies are converted into or adapted to use as an immuno-reagent

* * * * *